(12) United States Patent
Michaell

(10) Patent No.: US 6,695,784 B1
(45) Date of Patent: Feb. 24, 2004

(54) ULTRASOUND PULSATILITY IMAGING

(75) Inventor: David Michaell, Ashkelon (IL)

(73) Assignee: Inta-Medics, Ltd., Ashkelon (IL)

(*) Notice: Subject to any disclaimer, the term of this patent is extended or adjusted under 35 U.S.C. 154(b) by 0 days.

(21) Appl. No.: 09/936,030

(22) PCT Filed: Mar. 9, 2000

(86) PCT No.: PCT/IB00/00236
§ 371 (c)(1),
(2), (4) Date: Mar. 6, 2002

(87) PCT Pub. No.: WO00/57766
PCT Pub. Date: Oct. 5, 2000

(30) Foreign Application Priority Data

Mar. 9, 1999 (IL) ................................................ 128904

(51) Int. Cl.$^7$ ................................................ A61B 8/06
(52) U.S. Cl. ................................ 600/453; 128/916
(58) Field of Search .................... 600/437, 440–441, 600/443, 447, 453–456, 459; 128/916

(56) References Cited

U.S. PATENT DOCUMENTS

| | | | | |
|---|---|---|---|---|
| 5,628,321 A | * | 5/1997 | Scheib et al. | 600/454 |
| 5,720,291 A | * | 2/1998 | Schwartz | 128/916 |
| 5,860,924 A | * | 1/1999 | Quistgaard | 600/441 |
| 5,910,119 A | * | 6/1999 | Liu | 600/455 |
| 6,066,097 A | * | 5/2000 | Glenn et al. | 600/437 |
| 6,419,633 B1 | * | 7/2002 | Robinson et al. | 600/443 |
| 6,547,731 B1 | * | 4/2003 | Coleman et al. | 600/437 |

* cited by examiner

*Primary Examiner*—Francis J. Jaworski
(74) *Attorney, Agent, or Firm*—Davidson, Davidson & Kappel, LLC

(57) ABSTRACT

A method is provided for observing three-dimensional pulsatile activity in a volume of a subject's tissue, which includes activating an ultrasonic probes array (25) subset portion (20) having a curvature including focussing the ultrasound energy of probes (25) constituting a selected contiguous portion of the subarray in a selected portion of a selected slice of tissue (21) along a line, converting the reflected ultrasound energy to output signals and providing output data corresponding to the pulsatile activity, varying the focus of ultrasound energy along the line and repeating the converting and processing steps to thereby select additional lines within the selected slice, selecting additional subsets of the ultrasound array of probes so as to select additional slices within the volume, and performing tomographic analysis of the output data corresponding to pulsatile activity in the plurality of selected portions of tissue, so as to obtain a three dimensional image of pulsatile activity in the preselected volume of tissue.

13 Claims, 5 Drawing Sheets

ULTRASOUND PULSATILITY IMAGING

FIELD OF THE INVENTION

The present invention relates generally to the use of ultrasound to observe pulsatile activity in living tissue.

BACKGROUND OF THE INVENTION

Ultrasound imaging provides a non-invasive means to view internal portions of a patient's body, and so has proven a useful medical diagnostic tool. Ultrasound waves, typically of a frequency in the range of 2 to 20 MHz, are emitted into the body of the patient and reflected ultrasound waves from the body tissues are received and converted into signals which are processed to produce an image. These images, while usefull, have been limited in that they were two-dimensional and of low resolution. Recently, higher resolution and three-dimensional ultrasound images have become available, but without real-time imaging, as they require many measurements and significant data processing time to produce the images. Even advanced existing ultrasound imaging systems do not allow observation of pulsatile behavior, which can be a valuable diagnostic tool, in the tissue being examined.

A further limitation of existing ultrasound imaging systems is that the ultrasound waves they use undergo significant attenuation when passing through bone, which limits their usefulness for observing certain regions of the body, especially the brain.

U.S. Pat. No. 5,840,018, granted to the present inventor, discloses a method to perform realtime observations on blood vessels in the brain; the contents of this patent are incorporated herein by reference. It includes means and method for processing and analyzing time varying signals associated with pulsatile activity in blood vessels, especially by employing gating circuitry.

U.S. Pat. No. 4,549,533 discloses apparatus and method to generate and direct ultrasound energy over a predetermined region of the body, but the application disclosed therein is only for directing the ultrasound energy to the target region, without detecting reflected ultrasound energy to observe the target region.

U.S. Pat. No. 5,540,230 discloses apparatus and method employing ultrasound to determine the velocity of fluid flowing through a lumen. U.S. Pat. No. 5,394,750 discloses an ultrasound transceiver which includes filtering on received signals to reduce noise in detected signals and which may be employed to determine the velocity profile of blood flow in tissue. Both inventions disclosed therein only allow observation of a single point with no provision for multiple observations in real time.

U.S. Pat. No. 5,787,889 discloses a method and an ultrasound system for three-dimensional ultrasound imaging in real time, but is restricted to a physical image of the tissue being scanned, without observing pulsatility details. It is further limited by operator movement of the ultrasound transducer/receiver over the surface of the patient; indeed, the real-time imaging disclosed therein corresponds to tracking this manual probe movement. Further, ultrasound waves in the frequency range cited therein are subject to significant attenuation when passing through bone, resulting in the above mentioned limitation of applicability.

SUMMARY OF THE INVENTION

An aim of the present invention is to provide a method to image a volume of tissue in a subject with ultrasound waves that overcomes the limitations of the prior art by providing a dynamic three-dimensional representation and at a high resolution of pulsatile activity in the selected volume of tissue.

There is thus provided, in accordance with a preferred embodiment of the invention, a method for observing three-dimensional pulsatile activity in a preselected volume of tissue in a subject that includes the following steps:

placing an array of ultrasound probes in association with the surface of the subject, thereby selecting a discrete volume of tissue in the subject;

selecting a generally linear subset of the array, thereby defining a thin slice of the selected volume of tissue;

activating and focusing a selected contiguous portion, having a predetermined curvature, of the selected subset of the array of probes, so that each probe is operative:

to emit ultrasound waves in a preselected frequency waveband and at a preselected range of output intensities, typically with a bandwidth of substantially 0.4 MHz in the frequency range 0.4–40.0 MHz and an output intensity in the range 100–300 mW/cm$^2$, but especially in a waveband selected so as not to be substantially attenuated by bone, to receive reflected ultrasound energy from the tissue in the preselected frequency waveband, and to convert the received reflected ultrasound energy into output signals corresponding thereto;

and so that the focusing serves to select a portion of tissue along a line contained within the selected tissue slice which further intersects the linear subset of probes, the volume of the selected portion of the tissue slice defines the pixel size for the image that is desired to be produced, which is in the range 0.1 to 1.0 mm$^3$;

receiving, via the probes constituting the selected contiguous portion of the subarray of probes, the reflected ultrasound energy from the tissue and converting it into output signals corresponding to the reflected ultrasound energy;

processing these output signals from the probes so as to determine pulsatile activity in the selected portion of the selected tissue slice;

providing output data corresponding to the pulsatile activity in the selected portion of the selected tissue slice;

varying the focus of the ultrasound energy along the line within the volume slice and repeating above steps thereby scanning the selected line within the selected tissue slice and providing output data corresponding to the pulsatile activity in successive portions of tissue along the line;

selecting a sequence of contiguous portions of the selected subset of the array and repeating above steps thereby selecting a sequence of lines within the selected tissue slice, thereby scanning the selected tissue slice and providing output data corresponding to the pulsatile activity in successive portions of tissue along the lines within the slice;

selecting a sequence of subsets of the array of ultrasound probes and repeating above steps thereby selecting a sequence of slices within the selected tissue volume, thereby scanning the selected volume and providing output data corresponding to the pulsatile activity in successive slices of tissue within the volume; and performing tomographic analysis of the plurality of output data, thereby obtaining a three-dimensional image of the pulsatile activity in the selected volume of tissue.

Further in accordance with a preferred embodiment of the present invention, the sequence of slices within the selected tissue volume is a sequence of substantially parallel first slices, and the method further includes the following steps:

selecting additional linear subsets of the array of ultrasonic probes arranged in association with a second tissue slice having a non-parallel alignment with respect to the first tissue slices;

repeating the step of selecting a sequence of subsets of the array arranged in association with additional tissue slices parallel to the second tissue slice; and performing tomographic analysis of the plurality of output data, thereby obtaining a directional three-dimensional image of the pulsatile activity in the selected volume of tissue.

Before performing the tomographic analysis, additional linear subsets in association with subsequent tissue slices having non-parallel alignment with respect to both first and second tissue slices may further be selected. This, together with repetition of the step of selecting a sequence of subsets, provides more directional information to the three dimensional image of the pulsatile activity in the selected volume of tissue so obtained.

In accordance with the alternative preferred embodiments of the present invention, the step of activating and focusing may include changing the curvature of the selected contiguous portion of the linear subarray of ultrasound probes or adjusting the timing of the activation of the selected contiguous portion of the subarray of ultrasound probes, so as to focus the ultrasound energy variably within the selected tissue slice and to observe pulsatile activity therein. The frequency waveband of the ultrasound waves may also be varied.

Further in accordance with a preferred embodiment of the invention, the step of processing the output signals includes the substeps of:

converting the output signals into a summed output signal associated with the selected portion of the selected tissue slice;

measuring variation in the summed output signal as a function of time; and observing selected features of pulsatile activity in the time variation of the summed output signal associated with the selected portion of the selected tissue slice, typically by applying gating circuitry to the time variation.

Additionally in accordance with a preferred embodiment of the invention, the substep of observing selected features of pulsatile activity includes the substeps of:

performing spectral analysis of the summed output signal associated with the selected portion of the selected tissue slice to produce a frequency spectrum associated therewith;

selecting a reference pulsatile signal associated with the heart rate of the subject, such as an electrocardiogram signal;

performing spectral analysis of the reference pulsatile signal associated with the heart rate of the subject to produce a frequency spectrum associated therewith; and comparing the frequency spectrum of the summed output signal associated with the selected portion of the selected tissue slice with the frequency spectrum of the reference pulsatile signal.

BRIEF DESCRIPTION OF THE DRAWINGS

The present invention will be more fully understood and appreciated from the following detailed description, taken in conjunction with the drawings, in which.

DETAILED DESCRIPTION OF THE INVENTION

Referring now to FIGS. 1A through 5, there are shown an example of a system and details of its operation for observing three-dimensional pulsatile activity in a volume of tissue in a subject in accordance with a preferred embodiment of the present invention.

Figure 1A:
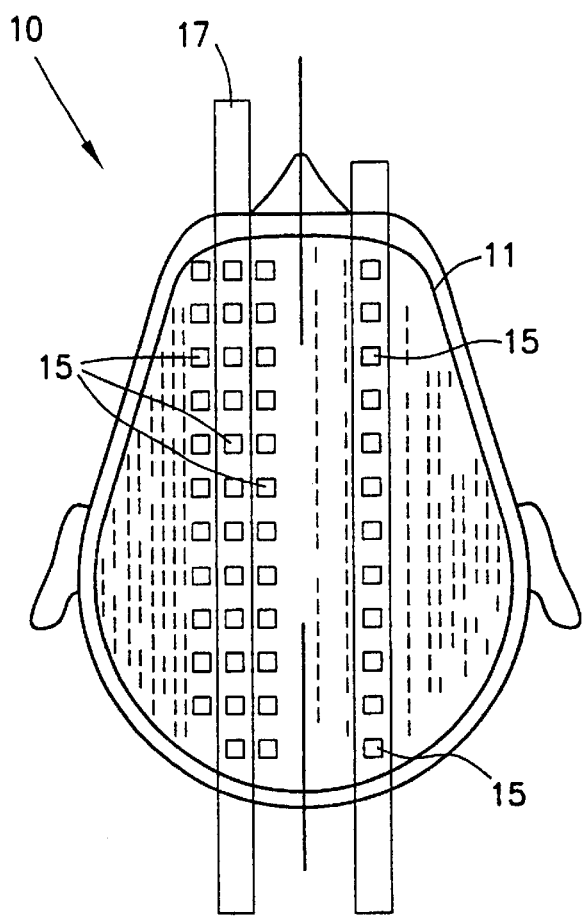
FIGS. 1A and 1B are two views of the head of a subject with an array of ultrasound probes in association therewith in accordance with a method which is a preferred embodiment of the present invention.
Figure 1B:
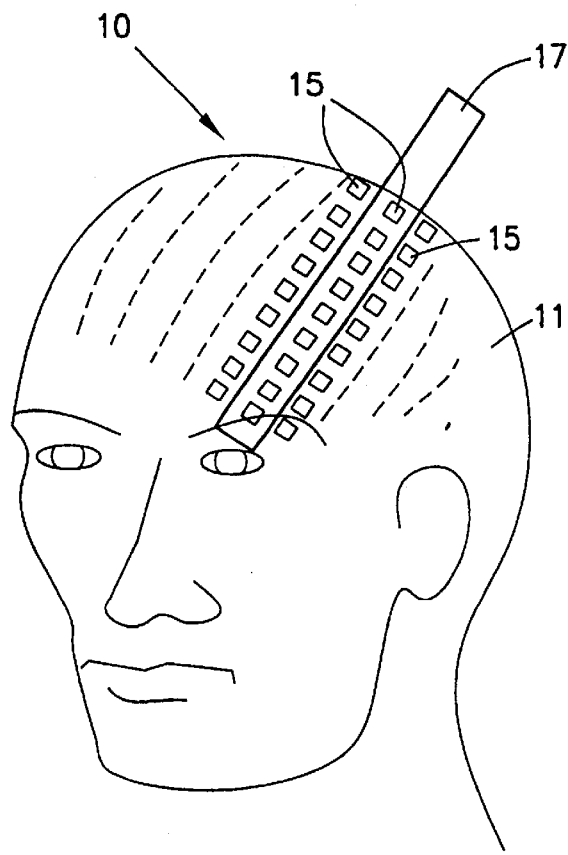

Referring now to FIGS. 1A and 1B, there are shown, by way of example, two views, overhead and transverse, of the head 11 of a subject with an array, referred to generally as 10, of ultrasound probes 15 arranged in association with the surface thereof, in accordance with a method which is a preferred embodiment of the present invention. Probes 15 are operative to emit ultrasound waves via the surface of the subject into a discrete volume of tissue in the subject, in the present example, the brain of the subject, and to detect reflected ultrasound energy therefrom. A thin slice of the tissue volume is defined by a selected generally linear subset of array 10 of probes 15 bordering thereon, indicated by box 17 in the drawings. In the present embodiment, probes 15 may be 2 mm×2 mm in size, and the slice may have a depth or thickness as small as 0.1 mm.

Figure 2:
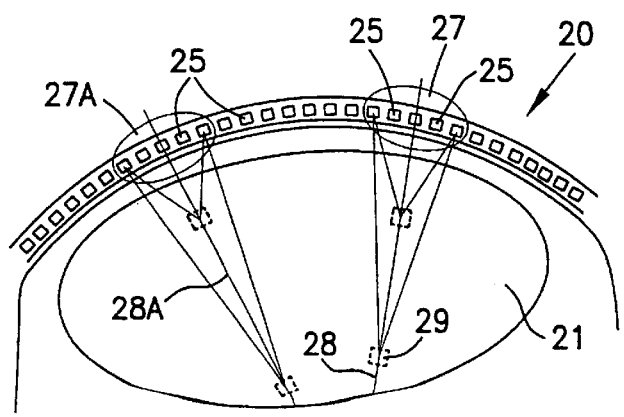
FIG. 2 is a view of a tissue slice of the subject and a subset of the array of ultrasound probes of FIG. 1.

Referring now to FIG. 2, there is shown tissue slice 21 surrounded by a subset, referred to generally as 20, of ultrasound probes 25. In subset 20, a contiguous group 27 of at least three probes 25, encircled in the drawing, representing a portion of subset 20, is activated to emit, into tissue slice 21, ultrasound waves in the frequency range 0.4–40.0 MHz with a typical bandwidth of approximately 0.4 MHz and an output intensity in the range 100–300 mW/cm$^2$. Probes 25 are further operative to detect reflected ultrasound energy from the tissue in slice 21. If, as in the present example, the tissue being observed is brain tissue, lower frequencies in the given range will, for a large portion of the population, reach the brain tissue with minimal attenuation passing through the bone of the skull.

As will be understood by persons skilled in the art, the curvature of the line connecting group 27 of probes produces a focusing effect with the ultrasound waves emitted thereby, wherein the ultrasound waves interfere constructively at a discrete location in the tissue being observed. It is worth noting that this constructive interference causes reflected ultrasound energy from the discrete location 29 in the tissue being observed to be of a magnitude significantly greater than that reflected from other locations in the tissue, thereby allowing reflected ultrasound energy from that location to be readily distinguished from that reflected from other locations, which may be referred to as "background" ultrasound energy. It is in this sense that it is meaningful to refer to observing the discrete location or focusing thereon. This effective focal point corresponds to a small portion 29 of the tissue, which falls on a line 28 in tissue slice 21 which intersects group 27 of probes, thereby defining the pixel volume for the observations, which, in accordance with a preferred embodiment of the present invention, can be a small as 0.1 mm$^3$.

Figure 3:
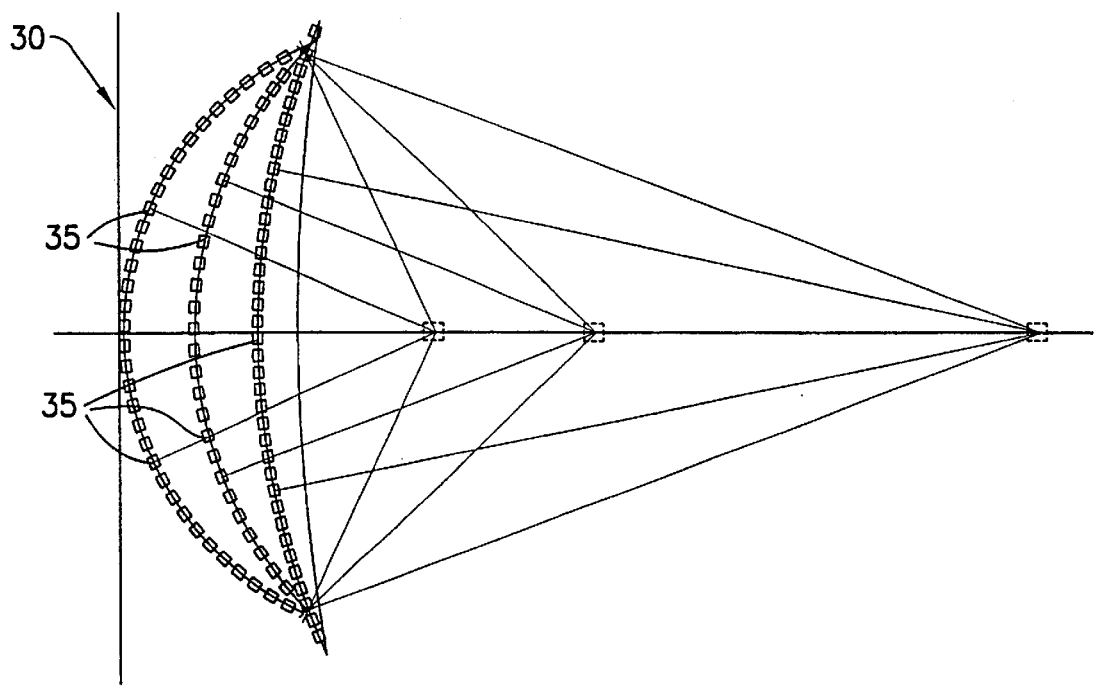
FIG. 3 is a schematic view of the step of varying the focus of a group of ultrasound probes in accordance with a preferred embodiment of the present invention.

Referring briefly to FIG. 3, there is shown the effect of slightly changing the positions of the probes constituting a group, referred to generally as 30, of probes 35 relative to one another, thereby varying the curvature of the line connecting them. As is shown in the drawing, as the curvature increases, the focus of the ultrasound waves emitted by group 30 of probes 35 becomes shorter, moving closer to the line of probes. Probes 35 may be moved to effect the change in curvature, for example, by individual piezoelectric actuators in association therewith.

As will be further understood by persons skilled in the art, change of focus can also be effected by controlling the timing of the ultrasound emission from the individual probes 35 of group 30 to produce the same constructive interference as that produced by curvature of group 30 of probes.

Returning now to FIG. 2, it can be seen that by suitably varying the focus of group 27 of probes, successive portions or pixels 29 of tissue can be selected for observation along line 28 covering its full extent within tissue slice 21. The drawing also shows a second group 27A of probes 25, which can be selectively activated in similar fashion to group 27 to allow observation along a second line 28A within tissue slice 21. By selecting successive groups of probes, a sequence of lines of pixels can be selected for observation to allow observation of tissue slice 21, pixel by pixel and line by line providing complete coverage thereof.

Referring again briefly to FIG. 1A, a series of generally parallel slices of the tissue volume can defined selecting successive generally linear subsets of array 10 of probes 15 to allow observation of the entire tissue volume, pixel by pixel, line by line, and slice by slice providing complete coverage thereof.

To summarize: by selection of successive generally linear subsets of probes from array 10, successive contiguous groups of probes 15 therewithin, and successive focal points thereof, a series of pixels within the tissue may observed which covers the entire volume of the tissue, at a resolution depending on the pixel size.

Figure 4:
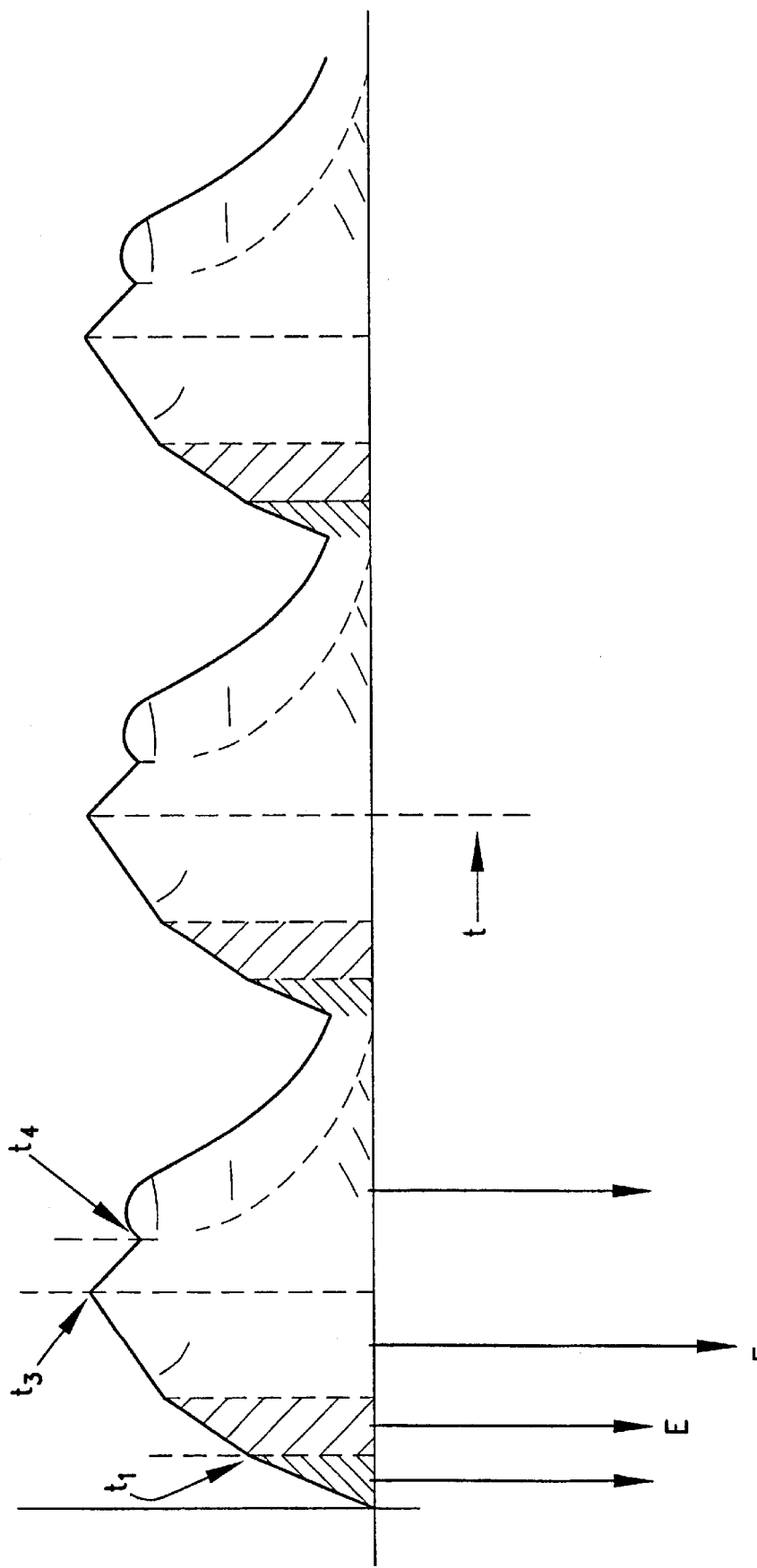
FIG. 4 is a graph of the time dependent signal observed in a portion of pulsing tissue.

Referring now to FIG. 4, there is shown a graph of the reflected ultrasound energy detected from a selected pixel in tissue exhibiting pulsatile activity as a function of time. The graph exhibits a periodic pulsing with a characteristic waveform with a number of identifiable segments and features, labeled $t_1$, $t_3$, $t_4$, and $E_B$, for example, in the drawing. As will be understood by persons skilled in the art, these can be used to identify specific structures within the tissue; for example, in the case of brain tissue, blood vessels and chambers known as ventricles may be identified by their observed pulsatile activity. In accordance with a method which is a preferred embodiment of the present invention, by applying gating circuitry to the time-dependent signal detected from the reflected ultrasound energy, a particular feature of the waveform or a parameter derived therefrom, such as its slope may be observed for all or a selected portion of pixels in the tissue.

In accordance with a method which is a further preferred embodiment of the present invention, spectral analysis may be performed on the time-dependent signal detected from the reflected ultrasound energy to produce a frequency spectrum associated therewith. By comparing the frequency spectrum associated with reflected ultrasound energy from selected tissue in the subject and the frequency spectrum produced by spectral analysis of any reference pulsatile signal associated with the heart rate of the subject, such as an electrocardiogram signal or any arterial pulse, useful diagnostic information may be obtained. In the present example, frequency shifts or offsets from the heart rate of the subject in the brain of the subject, can indicate migraine activity, edemas, or aneurysms.

By collecting and storing these sequences of observations in a suitably programmed data processing apparatus, the known method of tomographic analysis may be performed on the observations to produce an image of the three dimensional variation of the selected parameter in the tissue being observed.

Figure 5:
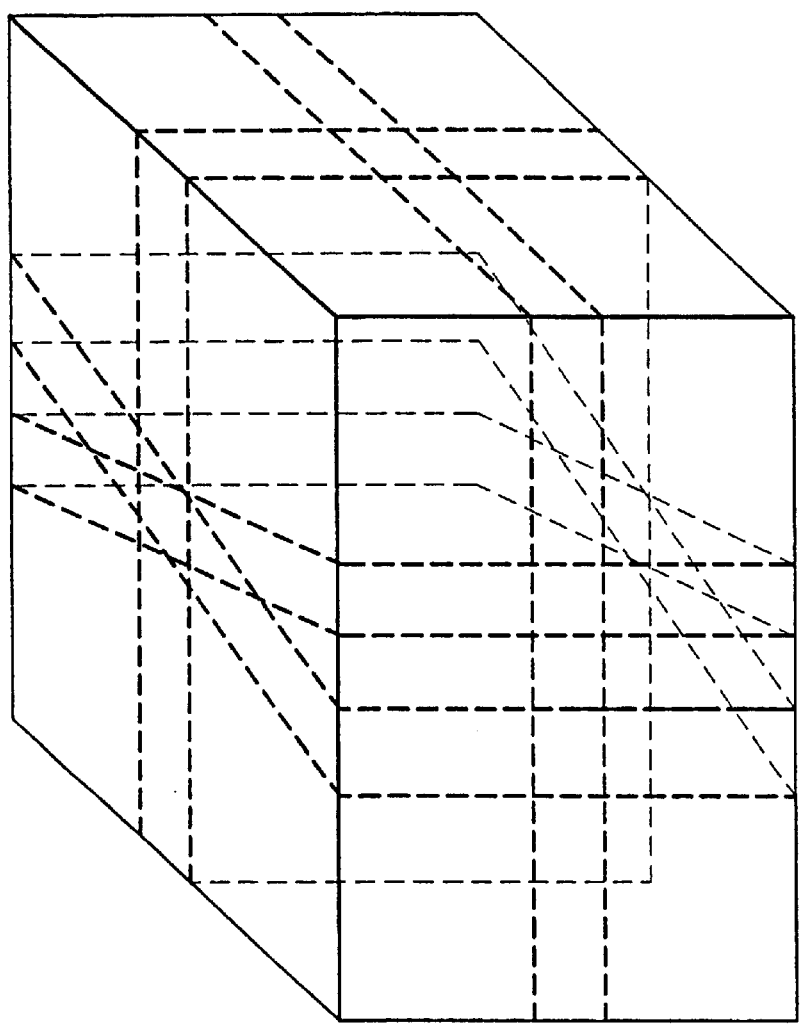
FIG. 5 a schematic view of multiply-oriented tissue slices in the same tissue sample of the subject of FIG. 1.

As will be understood by persons skilled in the art, some observations of pulsatile activity will vary with the orientation or direction of the observations. In some cases, change of orientation can optimize observation for more usable information, by increasing contrast in the resulting image; in other cases, what is observed has a three-dimensional or vectorial nature. Referring now to FIG. 5, there is shown a portion of tissue to be observed by the method of the present invention with a number of tissue slices with varying, non-parallel, orientations indicated therein. Pulsatile activity in the tissue in the varying directions may be observed by selecting suitable first subsets of an array of probes in association with the tissue. By further selecting a sequence of subsets parallel to the first sets, the entire volume of tissue may be observed. For example, observations may be made along three perpendicular axes to obtain full vectorial information about pulsatile activity in the tissue. This data may also be analyzed tomographically to produce a full, directional three-dimensional image of the pulsatile activity in the tissue.

Figure 6:
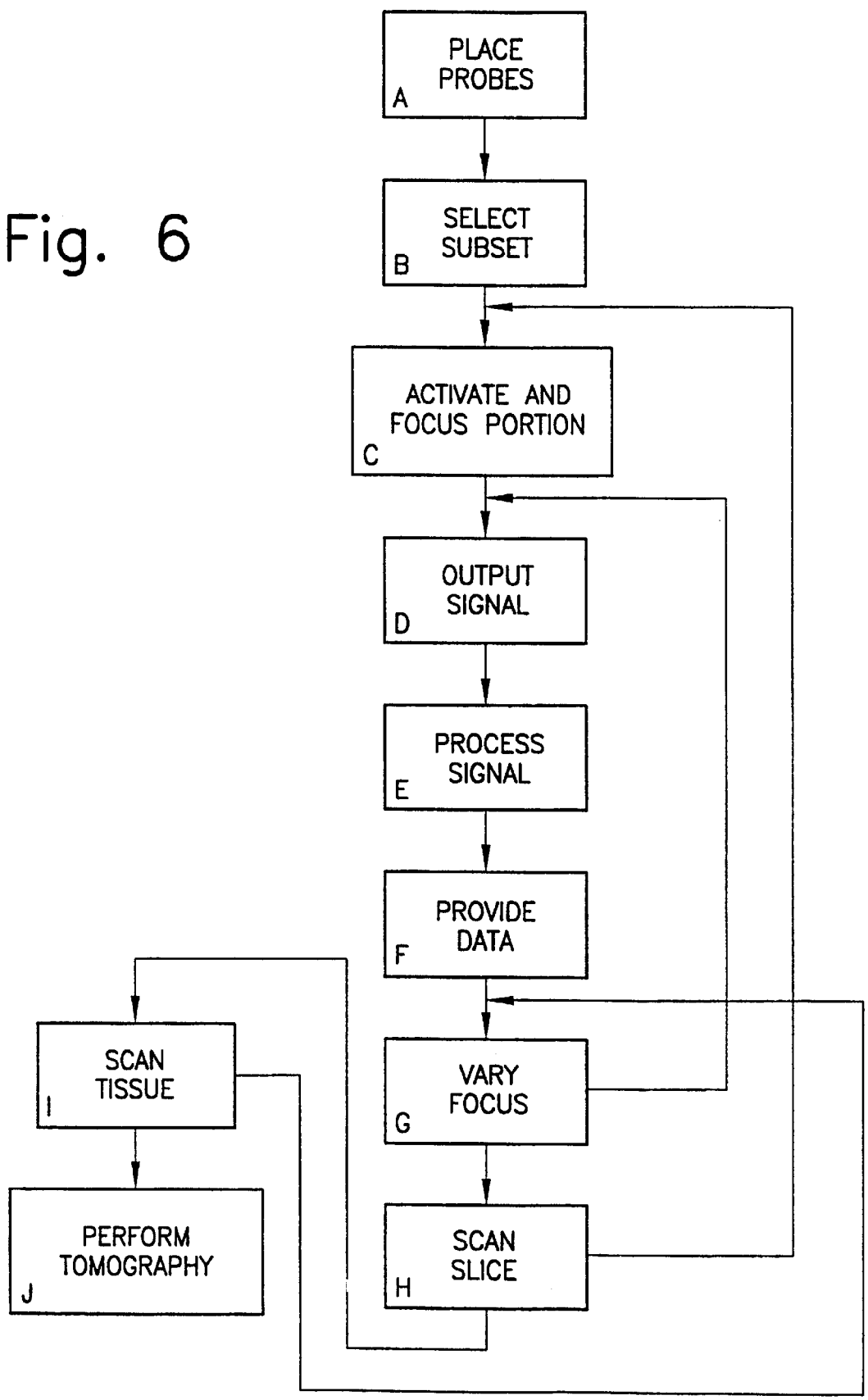
FIG. 6 is a flow chart of the method in accordance with a preferred embodiment of the present invention.

Referring now to FIG. 6, there is shown a flowchart for the method of the present invention. In the following discussion, steps of the method are referred to by letters in FIG. 6, and parts of a system to implement the method are referred to by numbers in FIGS. 1A through 5.

In accordance with a preferred embodiment of the present invention, a method for observing three-dimensional pulsatile activity in a volume of tissue in a subject of the present invention follows:

A. An array 10 of ultrasound probes 15 is placed in association with the surface of the subject, which serves to select a discrete volume of tissue in the subject; in the present example, the brain of the subject.

B. A generally linear subset of the array, indicated by box 17 in FIGS. 1A and 1B, is selected. This defines a thin slice of the selected volume of tissue, which, in the present embodiment, has a depth or thickness of approximately 1.0 mm.

C. A group of probes which is a selected contiguous portion of the selected subset of the array of probes, encircled and indicated by 27 in FIG. 2, is activated and focused. The activated probes are each operative:

to emit ultrasound waves in a preselected frequency waveband and at a preselected range of output intensities;

to receive reflected ultrasound energy from the tissue in the preselected frequency waveband, and to convert the received reflected ultrasound energy into an output signal.

In the present embodiment, the frequency waveband of the ultrasound waves emitted and received by the ultrasound probes has a bandwidth of substantially 0.4 MHz in the frequency range 0.4–40.0 MHz and the ultrasound waves are emitted with an output intensity in the range 100–300 mW/cm². Further, in particular for the present example wherein the selected tissue is brain tissue which is surrounded by the skull, the frequency waveband of the ultrasound waves emitted and received by the ultrasound probes is selected so as not to be substantially attenuated by bone tissue, which frequency waveband, it should be noted, may vary depending on the subject.

It should further be noted that the selected contiguous portion of the selected subset of the array of probes has a predetermined curvature which, as will be understood by those familiar with the art and as discussed above, will result in the ultrasound energy of the probes being focused in a selected portion 29 of the selected slice of tissue along a selected line 28 that is contained within the selected slice 21 and that intersects the linear subset of probes 20. The volume of the selected portion of the selected slice of tissue defines the pixel size for the image that is desired to be produced by the present method, which, in the present embodiment, is in the range 0.1 to 1.0 mm³.

D. Reflected ultrasound energy from the tissue is received by the probes and converted into output signals corresponding thereto.

E. The output signals from the probes are processed to determine pulsatile activity in the selected portion of the selected tissue slice. In accordance with a preferred embodiment of the present invention, this may include:

converting the output signals into a summed output signal associated with the selected portion of the selected tissue slice;

measuring variation in the summed output signal as a function of time; and observing selected features of pulsatile activity in the time variation of the summed output signal associated with the selected portion of the selected tissue slice, which may be accomplished by applying gating circuitry to the time variation of the summed output signal associated with the selected portion of the selected tissue slice. In accordance with a further preferred embodiment of the present invention, this may include:

performing spectral analysis of the summed output signal associated with the selected portion of the selected tissue slice to produce a frequency spectrum associated therewith;

selecting a reference pulsatile signal associated with the heart rate of the subject, which may be an electrocardiogram signal or any arterial pulse;

performing spectral analysis of the reference pulsatile signal associated with the heart rate of the subject to produce a frequency spectrum associated therewith; and comparing the frequency spectrum of the summed output signal associated with the selected portion of the selected tissue slice with the frequency spectrum of the reference pulsatile signal associated with the heart rate of the subject.

F. Output data corresponding to the pulsatile activity in the selected portion of the selected tissue slice is then provided and may be stored for later processing.

G. The focus of the ultrasound energy is varied along the selected line within the volume slice, and wherein the above steps:

(D.) reflected ultrasound energy from the tissue is received by the probes and converted into output signals corresponding thereto;

(E.) output signals from the probes are processed to determine pulsatile activity in the selected portion of the selected tissue slice; and (F.) output data corresponding to the pulsatile activity in the selected portion of the selected tissue slice is provided, are repeated for each of a sequence of pixels or selected portions of the selected volume slice along the full extent of the selected line within the volume slice. This scans the line completely, pixel by pixel, for pulsatile activity.

In a preferred embodiment of the present invention, the focus may be changed by changing the curvature of the selected contiguous portion of the linear subarray of ultrasound probes, as shown in FIG. 3, which may be effected, for example, by piezoelectric actuators in association with the individual probes. In an alternative embodiment of the present invention, the focus may be changed by adjusting the timing of the activation of at least a selected contiguous portion of the subarray of ultrasound probes. It is also possible to change the focus of the probes by varying the frequency waveband of the ultrasound waves they emit.

H. To scan the selected slice of tissue line by line, a sequence of contiguous portions of the selected subset of the array of probes is selected. For each member of the sequence, the above step (C.) wherein the group of probes which is the selected contiguous portion of the array of probes is activated and focused, the above steps (D.), (E.), and (F.) wherein output data corresponding to pulsatile activity in the selected portion 29 of the selected tissue slice 21 is provided, and the above step (G.) wherein the focus of the ultrasound energy is varied along the selected line within the volume slice are repeated. This produces output data corresponding to the pulsatile activity in the entire tissue slice.

I. To scan the entire selected volume of tissue slice by slice, a sequence of subsets of the array of ultrasonic probes is selected. For each member of the sequence, the above step (G) wherein a sequence of contiguous portions of the selected subset of the array of probes is selected is repeated. This produces output data corresponding to the pulsatile activity in the entire selected volume of tissue.

J. Finally, tomographic analysis of the entire plurality of output data is performed, so as to obtain a three dimensional image of pulsatile activity in the selected volume of tissue.

Further in accordance with a preferred embodiment of the present invention, the method may include an additional step, prior to the step (J.) wherein tomographic analysis is performed, wherein the selected volume of tissue is again scanned slice by slice, as in step (I) above, with this subsequent set of slices having a different, non-parallel, orientation with respect to the first set of slices. This may be accomplished by a suitable choice of a sequence of subsets of the array of ultrasonic probes. This may be repeated, for example, along three perpendicular axes to provide a directional or vectorial image of pulsatile activity in the selected tissue.

It will be appreciated by persons skilled in the art, that the scope of the present invention is not limited by what has been specifically shown and described hereinabove, merely by way of example. Rather, the scope of the present invention is defined solely by the claims, which follow.

What is claimed is:

1. A method for observing three-dimensional pulsatile activity in a preselected volume of tissue in a subject, the volume of tissue having a length, width, and depth, said method including the steps of:

placing an array of ultrasound probes in association with the surface of the subject;

selecting a generally linear subset of the array arranged in association with a selected slice of the preselected volume of tissue, said linear subset forming a subarray of said array of probes, wherein the selected slice has a length and a width, and at least a predetermined depth;

activating and focusing at least a selected contiguous portion of the selected subset of the array of probes, the selected contiguous portion of the selected subset of the array having a predetermined curvature, so that each probe is operative:

to emit ultrasound waves in a preselected frequency waveband and at a preselected range of output intensities, to receive reflected ultrasound energy from the tissue in the preselected frequency waveband, and to convert the received reflected ultrasound energy into output signals corresponding thereto;

and including focusing the ultrasound energy of the probes constituting the selected contiguous portion of the subarray of probes in a selected portion of the selected slice of tissue along a selected line, wherein the selected line is contained within the selected slice and intersects the linear subset of probes;

receiving, via the probes constituting the selected contiguous portion of the subarray of probes, the reflected ultrasound energy from the tissue and converting it into output signals corresponding to the reflected ultrasound energy;

processing the output signals from the probes constituting the selected contiguous portion of the subarray of probes so as to determine pulsatile activity in the selected portion of the selected tissue slice;

providing output data corresponding to the pulsatile activity in the selected portion of the selected tissue slice;

varying the focus of the ultrasound energy along the line within the volume slice and repeating said step of receiving and converting and said steps of processing and of providing for each of a sequence of selected portions of the selected tissue slice along the full extent of the selected line therewithin;

selecting a sequence of contiguous portions of the selected subset of the array and repeating for each of the selected sequence said step of activating and focusing, said step of receiving and converting, and said step of processing, further repeating for each selected portion of tissue said step of providing output data, and further repeating for each of the selected sequence said step of varying the focus; thereby to select additional lines within the selected slice and to determine pulsatile activity and to provide output data corresponding thereto along a multiplicity of selected lines along the full extent of the selected slice;

selecting a sequence of subsets of the array of ultrasound probes and repeating thereon said step of selecting a sequence of contiguous portions of the selected subset of the array, thereby to select additional slices within the preselected volume, so as to determine pulsatile activity and to provide output data corresponding thereto along a multiplicity of slices of tissue within the preselected volume along the full extent thereof; and performing tomographic analysis of the output data corresponding to pulsatile activity in the plurality of selected portions of tissue, so as to obtain a three dimensional image of pulsatile activity in the preselected volume of tissue.

2. A method according to claim 1 wherein the multiplicity of slices is a multiplicity of substantially parallel first slices, and said method further includes the steps of:

selecting additional linear subsets of the array of ultrasonic probes arranged in association with a second tissue slice having a non-parallel alignment with respect to the first tissue slices;

repeating said step of selecting a sequence of subsets of the array arranged in association with additional tissue slices parallel to the second tissue slice; and performing tomographic analysis of the output data corresponding to pulsatile activity in the plurality of selected portions of tissue, so as to obtain a directional three dimensional image of pulsatile activity in the preselected volume of tissue.

3. A method according to claim 2 wherein said method further includes the steps, prior to said step of performing tomographic analysis, of:

selecting further linear subsets of the array of ultrasonic probes arranged in association with subsequent tissue slices having a non-parallel alignment with respect to both first and second tissue slices; and repeating said step of selecting a sequence of subsets of the array arranged in association with additional tissue slices parallel to the second tissue slice.

4. A method according to claim 1 wherein said step of processing the output signals includes the subsets of:

converting the output signals into a summed output signal associated with the selected portion of the selected tissue slice;

measuring variation in the summed output signal as a function of time; and observing selected features of pulsatile activity in the time variation of the summed output signal associated with the selected portion of the selected tissue slice.

5. A method according to claim 4 wherein said substep of observing selected features of pulsatile activity includes the substep of applying gating circuitry to the time variation of the summed output signal associated with the selected portion of the selected tissue slice.

6. A method according to claim 4 wherein said substep of observing selected features of pulsatile activity includes the substeps of:

performing spectral analysis of the summed output signal associated with the selected portion of the selected tissue slice to produce a frequency spectrum associated therewith;

selecting a reference pulsatile signal associated with the heart rate of the subject;

performing spectral analysis of the reference pulsatile signal associated with the heart rate of the subject to produce a frequency spectrum associated therewith; and comparing the frequency spectrum of the summed output signal associated with the selected portion of the selected tissue slice with the frequency spectrum of the reference pulsatile signal associated with the heart rate of the subject.

7. A method according to claim 6 wherein the reference pulsatile signal associated with the heart rate of the subject is an electrocardiogram signal.

8. A method according to claim 1 wherein said step of activating and focusing includes the substep of changing the curvature of the selected contiguous portion of the linear subarray of ultrasound probes, so as to focus the ultrasound energy variably within the selected tissue slice and to observe pulsatile activity therein.

9. A method according to claim 1 wherein said step of activating and focusing includes the substep of adjusting the timing of the activation of at least a selected contiguous portion of the subarray of ultrasound probes, so as to focus the ultrasound energy variably within the selected tissue slice and to observe pulsatile activity therein.

10. A method according to claim 1 wherein said step of activating and focusing includes the substep of varying the selected frequency waveband of the ultrasound waves emitted and received by the ultrasound probes.

11. A method according to claim 1 wherein the frequency waveband of the ultrasound waves emitted and received by the ultrasound probes is selected so as not to be substantially attenuated by bone tissue.

12. A method according to claim 1 wherein the frequency waveband of the ultrasound waves emitted and received by the ultrasound probes has a bandwidth of substantially 0.4 MHz in the frequency range 0.4–30.0 MHz and wherein the output intensity is in the range 100–300 mW/cm$^2$.

13. A method according to claim 1 wherein the selected portion of the selected slice of tissue has a volume in the range 0.1 to 1.0 mm$^3$.

* * * * *